United States Patent [19]
Lassila et al.

[11] Patent Number: 6,015,852
[45] Date of Patent: *Jan. 18, 2000

[54] SURFACE TENSION REDUCTION WITH ALKYLATED HIGHER POLYAMINES

[75] Inventors: Kevin Rodney Lassila, Macungie; Kristen Elaine Minnich; Richard Van Court Carr, both of Allentown, all of Pa.

[73] Assignee: Air Products and Chemicals, Inc., Allentown, Pa.

[*] Notice: This patent is subject to a terminal disclaimer.

[21] Appl. No.: 08/968,222

[22] Filed: Nov. 12, 1997

[51] Int. Cl.$^7$ ............................................. C08J 3/03
[52] U.S. Cl. .................... 524/251; 524/252; 528/422; 523/160; 523/161; 428/420; 428/423.1; 428/524; 427/411; 106/31.64; 106/31.75; 106/31.89
[58] Field of Search ................................ 428/420, 423.1, 428/524; 524/251, 252; 523/160, 161; 427/411; 106/31.64, 31.75, 31.89; 528/422

[56] References Cited

U.S. PATENT DOCUMENTS

| | | | |
|---|---|---|---|
| 2,267,205 | 12/1941 | Kyrides et al. | 528/422 |
| 4,126,640 | 11/1978 | Floyd | 260/583 P |
| 4,195,152 | 3/1980 | Floyd | 528/87 |
| 5,098,478 | 3/1992 | Krishman et al. | 106/23 |
| 5,562,762 | 10/1996 | Mrvos et al. | 106/22 |

OTHER PUBLICATIONS

Schwartz, J., "The Importance of Low Dynamic Surface Tension in Waterborne Coatings" Journal of Coating Technology, Sep. 1992.

Murata, Y., Ueda, M., "Antimicrobal Property of N–alkyldiethylenetriamines and N–acyldiethylenetriamines Against Some Dental Plaque Bacteria" Soc. Antibact. Antifung. Agents, Jpn., 1989.

Wirth, W., Storp, S. and Jacobnson, W., "Mechanisms Controlling Leaf Retention of Agricultural Spray Solutions", Pestic. Sci. 1991, 33, 411–420.

Medina, S. W. Sutovich, "Using Surfactants to Formulate VOC Compliant Waterbased Inks" Am. Ink Maker 1994, 72 (2) 32–38.

*Primary Examiner*—Duc Truong
*Attorney, Agent, or Firm*—Michael Leach

[57] ABSTRACT

This invention provides water-based compositions, particularly coating, ink, and agricultural compositions, manifesting reduced equilibrium and dynamic surface tension by the incorporation of a surface tension reducing amount of certain alkylated polyamine compounds of the structures I and II $$RHN{-}[(CH_2)_n NH]_p{-}(CH_2)_n NHR \qquad\qquad I$$

where the R groups are independently hydrogen or C5 to C8 alkyl, provided that at least one R is not hydrogen; n is 2 to 6 and p is 2 to 8, and

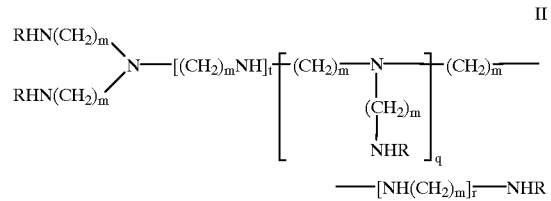

where the R groups are independently hydrogen or C5 to C8 alkyl, provided at least one R is not hydrogen, m is 2 to 6, t is 0 to 3, q is 0 to 3, and r is 0 to 5.

24 Claims, No Drawings

# SURFACE TENSION REDUCTION WITH ALKYLATED HIGHER POLYAMINES

FIELD OF THE INVENTION

The invention relates to the use of alkylated polyamines to reduce the surface tension in water-based systems.

BACKGROUND OF THE INVENTION

The ability to reduce the surface tension of water is of great importance in waterborne coatings, inks, adhesives, and agricultural formulations because decreased surface tension translates to enhanced substrate wetting in actual formulations. Surface tension reduction in water-based systems is generally achieved through the addition of surfactants. Performance attributes resulting from the addition of surfactants include enhanced surface coverage, fewer defects, and more uniform distribution. Equilibrium surface tension performance is important when the system is at rest. However, the ability to reduce surface tension under dynamic conditions is of great importance in applications where high surface creation rates are utilized. Such applications include spraying of coatings or agricultural formulations, or high speed gravure or ink-jet printing. Dynamic surface tension is a fundamental quantity which provides a measure of the ability of a surfactant to reduce surface tension and provide wetting under such high speed application conditions.

Traditional nonionic surfactants such as alkylphenol or alcohol ethoxylates, and ethylene oxide (EO) propylene oxide (PO) copolymers have excellent equilibrium surface tension performance but are generally characterized as having poor dynamic surface tension reduction. In contrast, certain anionic surfactants such as sodium dialkyl sulfosuccinates can provide good dynamic results, but these are very foamy and impart water sensitivity to the finished coating.

The objective of this invention is to provide a family of surfactants which provide good equilibrium and dynamic surface tension properties and are low-foaming and would be widely accepted in the coating, ink, adhesive, and agricultural formulation industries.

The importance of reducing equilibrium and dynamic surface tension in applications such as coatings, inks, and agricultural formulations is well-appreciated in the art.

Low dynamic surface tension is of great importance in the application of waterborne coatings. In an article, [Schwartz, J. "The Importance of Low Dynamic Surface Tension in Waterborne Coatings", Journal of Coatings Technology, September 1992] there is a discussion of surface tension properties in waterborne coatings and a discussion of dynamic surface tension in such coatings. Equilibrium and dynamic surface tension were evaluated for several surface active agents including the ethylene oxide adducts of acetylenic glycols. It is pointed out that low dynamic surface tension is an important factor in achieving superior film formation in waterborne coatings. Dynamic coating application methods require surfactants with low dynamic surface tensions in order to prevent defects such as retraction, craters, and foam.

Efficient application of agricultural products is also highly dependent on the dynamic surface tension properties of the formulation. In an article, [Wirth, W.; Storp, S.; Jacobsen, W. "Mechanisms Controlling Leaf Retention of Agricultural Spray Solutions"; Pestic. Sci, 1991, 33, 411–420], the relationship between the dynamic surface tension of agricultural formulations and the ability of these formulations to be retained on a leaf was studied. These workers observed a good correlation between retention values and dynamic surface tension, with more effective retention of formulations exhibiting low dynamic surface tension.

Low dynamic surface tension is also important in high-speed printing as discussed in the article "Using Surfactants to Formulate VOC Compliant Waterbased Inks" [Medina, S. W.,; Sutovich, M. N. Am. Ink Maker 1994, 72 (2), 32–38]. In this article, it is stated that equilibrium surface tensions (EST's) are pertinent only to ink systems at rest. EST values, however, are not good indicators of performance in the dynamic, high speed printing environment under which the ink is used. Dynamic surface tension is a more appropriate property. This dynamic measurement is an indicator of the ability of the surfactant to migrate to a newly created ink/substrate interface to provide wetting during high speed printing.

U.S. Pat. No. 5,098,478 discloses water-based ink compositions comprising water, a pigment, a nonionic surfactant and a solubilizing agent for the nonionic surfactant. Dynamic surface tension in ink compositions for publication gravure printing must be reduced to a level of about 25 to 40 dynes/cm to assure that printability problems will not be encountered.

U.S. Pat. No. 5,562,762 discloses an aqueous jet ink of water, dissolved dyes and a tertiary amine having two polyethoxylate substituents and that low dynamic surface tension is important in ink jet printing.

Although there have been numerous references to alkylated polyamines, it has not been recognized that such materials have the ability to reduce dynamic surface tension of aqueous solutions while contributing little foam to the system. This combination of properties would be of value in water-based coatings, inks, adhesives, and agricultural formulations. The following patents and publications relate to alkylated polyethyleneamines and their applications:

U.S. Pat. No. 4,126,640 and U.S. Pat. No. 4,195,152 disclose N—(C5–C8)alkyl polyamines, e.g., MIBK and MIAK reductive alkylates of diethylenetriamine:

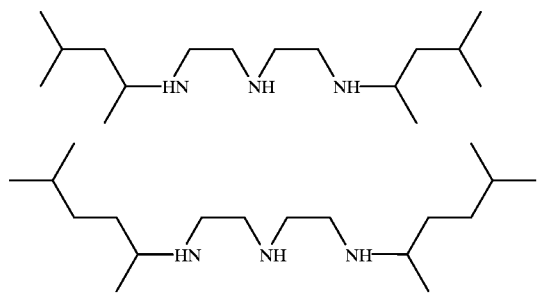

These materials are noted to be useful as curatives in high solids epoxy coatings because of their very low viscosity. Other suggested uses are in potting compositions, laminations, and adhesives.

Y. Murata and M. J. Ueda, Antibact. Antifung. Agents 1989, 17 (8), 371–375 disclose trihydrochlorides of N,N"-dialkyldiethylenetriamines of the form

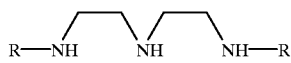

where R is a linear C8 or C10 alkyl group have been shown to have antimicrobial properties against dental plaque bacteria. This study showed that in vitro bactericidal activity tended to increase with the length of the N-substituted alkyl chain. These workers suggested that this phenomenon may mean that each compound acts as a cationic surfactant. There is no suggestion that these materials should be effective at reducing dynamic surface tension. Furthermore, there is no suggestion that the free bases should have any effect reducing either equilibrium or dynamic surface tension.

SUMMARY OF THE INVENTION

This invention provides water-based compositions containing an organic compound, particularly organic coating, ink, and agricultural compositions, having reduced equilibrium and dynamic surface tension by incorporation of an effective amount of at least one alkylated polyamine compound of structures I and II:

RHN—[(CH$_2$)$_n$NH]$_p$—(CH$_2$)$_n$NHR  I where the R groups are independently hydrogen or C5 to C8 alkyl, provided that at least one R is not hydrogen; n is 2 to 6 and p is 2 to 8, and

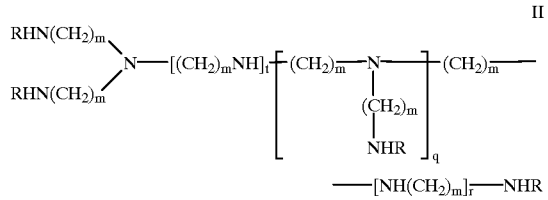

where the R groups are independently hydrogen or C5 to C8 alkyl, provided at least one R is not hydrogen, m is 2 to 6, t is 0 to 3, q is 0 to 3, and r is 0 to 5.

Also provided is a method for applying a water-based organic compound-containing composition to a surface, especially to partially or fully coat the surface with the water-based composition, the composition containing an effective amount of an alkylated polyamine compound of the above structure for reducing the dynamic surface tension of the water-based composition.

There are significant advantages associated with the use of these alkylated polyamines in water-based organic coatings, inks, and agricultural compositions and these advantages include:

- an ability to formulate water-borne coatings, inks, and agricultural compositions which may be applied to a variety of substrates with excellent wetting of substrate surfaces including contaminated and low energy surfaces;
- an ability to provide a reduction in coating or printing defects such as orange peel and flow/leveling deficiencies;
- an ability to produce water-borne coatings and inks which have low volatile organic content, thus making these surfactants environmentally favorable;
- an ability to formulate coating and ink compositions capable of high speed application;
- an ability to formulate compositions which retain dynamic surface tension properties under strongly basic, high temperature environments.

Because of their excellent surfactant properties and low foam characteristics, these materials are likely to find applicability in many applications in which reduction in dynamic and equilibrium surface tension and low foam are important. Such applications include various wet-processing textile operations, such as dyeing of fibers, fiber souring, and kier boiling, where low-foaming properties would be particularly advantageous; they may also have applicability in soaps, water-based perfumes, shampoos, and various detergents where their marked ability to lower surface tension while simultaneously producing substantially no foam would be highly desirable.

DETAILED DESCRIPTION OF THE INVENTION

This invention relates to the use of compounds of the following formulas I and II

RHN—[(CH$_2$)$_n$NH]$_p$—(CH$_2$)$_n$NHR  I where the R groups are independently hydrogen or C5 to C8 alkyl, provided that at least one R is not hydrogen; n is 2 to 6 and p is 2 to 8; preferably R is C5 to C8 alkyl, n is 2 or 3 and p is 2 to 5, especially 2 or 3; and

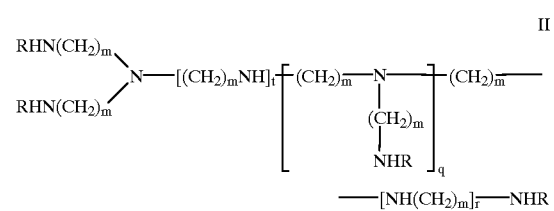

where the R groups are independently hydrogen or C5 to C8 alkyl, provided at least one R is not hydrogen, m is 2 to 6, t is 0 to 3, q is 0 to 3, and r is 0 to 5, preferably R is C5 to C8 alkyl, m is 2 or 3, t is 0 or 1, q is 0 to 2 and r is 0 to 3, for the reduction of equilibrium and dynamic surface tension in water-based compositions containing an organic compound.

It is desirable that an aqueous solution of the alkylated polyamine demonstrates a dynamic surface tension of less than 45 dynes/cm at a concentration of ≦5 wt % in water at 23° C. and 1 bubble/second according to the maximum-bubble-pressure method. The maximum-bubble-pressure method of measuring surface tension is described in *Langmuir* 1986, 2, 428–432, which is incorporated by reference.

The alkylated polyamines can be prepared by reductive alkylation of polyamines with aldehydes and ketones using well-established procedures. The essential aspects of the preparation are the reaction of an aldehyde or ketone with the polyamine to make an imine or enamine intermediate which then reacts with hydrogen in the presence of a suitable hydrogenation catalyst to form the corresponding saturated derivative.

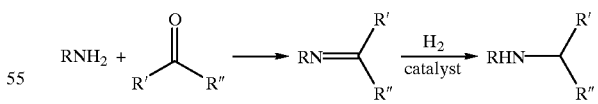

The imine or enamine derivative may be preformed or may be prepared in situ. The reductive alkylation procedure is the method of choice for the production of these materials, but the products may also be prepared by reaction of a polyamine derivative with an alkyl halide, or by reaction of a polyamine with an alcohol in the presence of a suitable catalyst, all being syntheses well known to an organic chemist.

Polyamine starting materials which are suitable for the preparation of the compounds of this invention include polyalkyleneamines, e.g., polyethyleneamines such as tri-ethylenetetramine (TETA), tris-(2-aminoethyl)amine, tetra-ethylenepentamine (TEPA) and polypropyleneamines such as tris-(3-aminopropyl)amine (TAPA), as well as mixtures containing substantial quantities of these materials which are commonly available. Polyamine starting materials containing three-carbon linking groups may be prepared by reaction of acrylonitrile with suitable di- or polyamines, followed by hydrogenation:

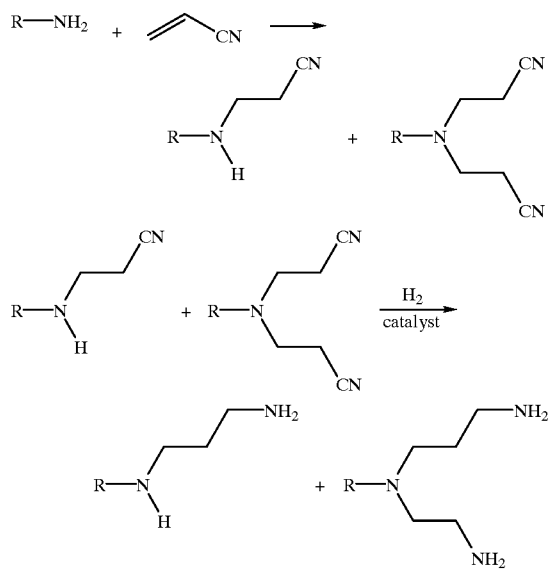

where $RNH_2$ represents a di- or polyamine, and it is understood that other active-hydrogen-containing amine groups in the molecule may also undergo the cyanoethylation reaction. Diamines suitable for the practice of the aminopropylation process include 1,2-ethylenediamine, 1,3-propanediamine, 1,2-propanediamine, 1,4-butanediamine, 1,5-pentanediamine, 2-methyl-1,5-pentanediamine, and 1,6-hexanediamine, and so on. Polyamines suitable for the practice of the aminopropylation process include diethylenetriamine (DETA), diaminopropylamine (DAPA), triethylenetetramine (TETA), tris-2-aminoethylamine (TAEA), and so on.

Alkyl groups which are suitable for use in this invention should have sufficient carbon atoms to confer surface activity (i.e. an ability to reduce the surface tension of water) to the material but not enough carbon atoms to decrease the solubility to the extent that the ability of the material to reduce surface tension is insufficient for a particular application. In general, an increase in the carbon number increases the efficiency of the resulting alkylated polyamine surfactant (i.e., less surfactant is required to obtain a given decrease in surface tension) but decreases its ability to reduce surface tension at high surface creation rates (i.e., less effective for reducing dynamic surface tension). The latter effect is a result of the fact that increased carbon number generally decreases the water solubility of the material, and consequently, diminishes the diffusive flux of surfactant to newly-created surface. Generally, in the practice of this invention, it is desirable to use alkylated polyamines having a solubility in water of at least 0.005 wt %, preferably from 0.01 to 2 wt %, and most preferably from 0.05 to 1.5 wt %.

The alkyl groups may be the same or different. They may be linear or branched, and the point of attachment to the nitrogen of the polyamine may be on either an internal or terminal carbon. Suitable alkyl groups are derived from reductive alkylation reactions of a C5 to C8 aldehyde or ketone, preferably derived from reductive alkylation reactions of methyl isobutyl ketone or methyl isoamyl ketone. Specific examples of suitable C5 to C8 aldehydes and ketones include 1-pentanal, 2-pentanone, 3-pentanone, methyl isopropyl ketone, 1-hexanal, 2-hexanone, 3-hexanone, methyl tert-butyl ketone, ethyl isopropyl ketone, 1-heptanal, 2-methylhexanal, 2-heptanone, 3-heptanone, 4-heptanone, 1-octanal, 2-octanone, 3-octanone, 4-octanone, 2-ethylhexanal, and so on. The specific carbonyl compound chosen and the number attached to the polyamine derivative will depend on the surfactant properties required for a particular application.

An amount of the alkylated polyamine compound that is effective to reduce the equilibrium and/or dynamic surface tension of the water-based, organic compound-containing composition is added. Such effective amount may range from 0.001 to 20 g/100 ml, preferably 0.01 to 2 g/100 ml, of the aqueous composition. Naturally, the most effective amount will depend on the particular application and the solubility of the alkylated polyamine.

In the following water-based organic coating, ink, and agricultural compositions containing an alkylated polyamine according to the invention, the other listed components of such compositions are those materials well known to the workers in the relevant art.

A typical water-based organic coating composition to which the alkylated polyamine surfactants of the invention may be added would comprise the following components in an aqueous medium at 30 to 80% solids:

| Typical Water-Based Organic Coating Composition | |
|---|---|
| 0 to 50 wt % | Pigment Dispersant/Grind Resin |
| 0 to 80 wt % | Coloring Pigments/Extender Pigments/Anti-Corrosive Pigments/Other Pigment Types |
| 5 to 99.9 wt % | Water-Borne/Water-Dispersible/Water-Soluble Resins |
| 0 to 30 wt % | Slip Additives/Antimicrobials/Processing Aids/Defoamers |
| 0 to 50 wt % | Coalescing or Other Solvents |
| 0.01 to 10 wt % | Surfactant/Wetting Agent/Flow and Leveling Agents |
| 0.01 to 5 wt % | Alkylated Polyamine |

A typical water-based ink composition to which the alkylated polyamine surfactants of the invention may be added would comprise the following components in an aqueous medium at 20 to 60% solids:

| Typical Water-Based Ink Composition | |
|---|---|
| 1 to 50 wt % | Pigment |
| 0 to 50 wt % | Pigment Dispersant/Grind Resin |
| 0 to 50 wt % | Clay base in appropriate resin solution vehicle |
| 5 to 99.9 wt % | Water-Borne/Water-Dispersible/Water-Soluble Resins |
| 0 to 30 wt % | Coalescing Solvents |
| 0.01 to 10 wt % | Surfactant/Wetting Agent |
| 0.01 to 10 wt % | Processing Aids/Defoamers/Solubilizing Agents |
| 0.01 to 5 wt % | Alkylated Polyamine |

A typical water-based agricultural composition to which the alkylated polyamine surfactants of the invention may be added would comprise the following components in an aqueous medium at 0.1 to 80% ingredients.

| Typical Water-Based Agricultural Composition | |
|---|---|
| 0.1 to 50 wt % | Pesticide or Plant Growth Modifying Agent |
| 0.01 to 10 wt % | Surfactant |
| 0 to 5 wt % | Dyes |
| 0 to 20 wt % | Thickeners/Stabilizers/Co-surfactants/Gel Inhibitors/Defoamers |
| 0 to 25 wt % | Antifreeze |
| 0.1 to 50 wt % | Akylated Polyamine |

EXAMPLE 1

This example illustrates the procedure for the preparation of the reductive alkylation product of a mixture of polyethylene polyamines and methyl isoamyl ketone.

A mixed polyamine stream (Union Carbide TPH Amines) containing linear and branched triethylene tetramine, tetraethylene pentamine and pentaethylene hexamine (100 g, approximately 0.4 mole), methyl isoamyl ketone (103, 0.9 mole) and 10% Pd/C (4 wt % of total charge) were charged to a one liter stainless steel autoclave. The reactor was sealed and purged with nitrogen then hydrogen. The contents of the reactor were heated to 90° C. under 7 bar (100 psig) hydrogen. The pressure was increased to 55 bar (800 psig) and maintained throughout the reaction (5 hr) by admission of hydrogen from a one gallon ballast on demand by a dome regulator. The excess methyl isoamyl ketone was removed in vacuo following the addition of 100 g of water. The final product (184 g) contained 7.4 wt % water by Karl Fischer titration and was used without further purification.

EXAMPLE 2

This example illustrates the procedure for the preparation of the reductive alkylation product of a mixture of higher polyethylene polyamines and methyl isoamyl ketone.

A mixed polyamine stream (Union Carbide HPA-X) containing linear and branched diethylene triamine, triethylene tetramine, tetraethylene pentamine, pentaethylene hexamine, hexaethylene heptamine and heptaethylene octamine (100 g, approximately 0.4 mole), methyl isoamyl ketone (103 g, 0.9 mole) and 10% Pd/C (4 wt % of total charge) were charged to a one liter stainless steel autoclave and reacted as in Example 1 for 5 hours. The excess methyl isoamyl ketone was removed in vacuo following the addition of 100 g of water. The final product (178 g) contained 13.8 wt % water by Karl Fischer and was used without further purification.

EXAMPLE 3

This example illustrates the preparative procedure for the reductive alkylation product of a triethylenetetramine and methyl isobutyl ketone (TETA/MIBK). The triethylenetetramine starting material was a commercially available mixture containing ca. 66% linear and 4% branched TETA

 and

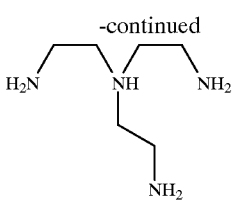

and 11% and 17%, respectively, of the cyclic materials

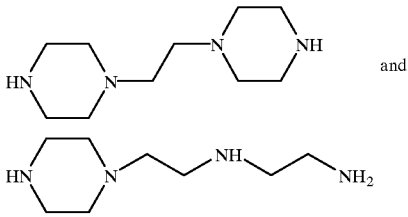

The triethylenetetramine-containing mixture (0.8 mole), methyl isobutyl ketone (1.5 mole) and 10% Pd/C (4 wt % of total charge) were charged to a one liter stainless steel autoclave and reacted as in Example 1 for 6 hours. The reactor contents were analyzed by GC/FID and found to be 4.2 area % monoalkylated, 83.6 area % dialkylated and 7.1 area % trialkylated derivatives of the triethylenetetramine mixture which can be represented as a mixture of the structures

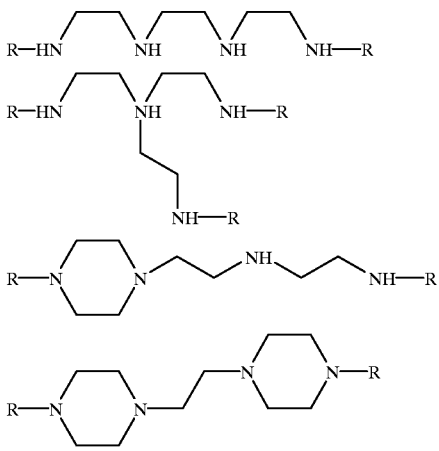

where R=H or —$CH(CH_3)CH_2CH(CH_3)_2$.

The product was distilled at 128–140° C., 0.07 millibar (0.05 Torr) to provide a material with a composition essentially unchanged from that described above.

In the following examples dynamic surface tension data were generated for aqueous solutions of the indicated compounds using the maximum-bubble-pressure method at the indicated bubble rates, i.e., bubbles/second (b/s), and room temperature of about 23° C. The equipment used was a Kruss BP 2 bubble pressure tensiometer.

EXAMPLE 4

Solutions in distilled water of the reductive alkylation product of Amine TPH and methyl isoamyl ketone (TPH/MIAK; Example 1) were prepared and their dynamic surface tension properties were measured using the maximum bubble pressure procedure previously referenced. Dynamic surface tension data were obtained for various aqueous solutions of the TPH/MIAK using the maximum bubble pressure method at bubble rates from 0.1 to 20 b/s. These data provide information about the performance of a surfactant at conditions from near-equilibrium (0.1 b/s) through extremely high surface creation rates (20 b/s). In practical terms, high bubble rates correspond to high printing speeds in lithographic or ink-jet printing, high spray or roller velocities in coating applications, and rapid application rates for agricultural products.

The data are set forth in Table 1. Concentrations are tabulated on a 100% active basis.

TABLE 1

| Concentration | TPH/MIAK. | | | | |
|---|---|---|---|---|---|
| | Dynamic Surface Tension (dyne/cm) | | | | |
| (wt %) | 0.1 b/s | 1 b/s | 6 b/s | 15 b/s | 20 b/s |
| 0.03 | 30.6 | 39.9 | 52.4 | 58.5 | 58.9 |
| 0.05 | 29.0 | 34.9 | 46.0 | 52.1 | 52.3 |
| 0.07 | 28.0 | 31.2 | 42.5 | 48.6 | 49.6 |
| 0.1 | 27.3 | 29.7 | 39.7 | 45.0 | 46.4 |
| 0.2 | 26.2 | 27.1 | 33.6 | 38.2 | 34.1 |

These results show that the reductive alkylation product of Amine TPH and methyl isoamyl ketone exhibited an outstanding ability to reduce the surface tension of water under conditions of both high and low surface creation rate, and that the material was very efficient at reducing the surface tension of water. The low amounts of this material required to provide a reduction in surface tension would positively impact the economics of coating, ink, and agricultural formulations. Furthermore, use of lower surfactant quantities would also reduce emissions of volatile organic compounds from these formulations.

EXAMPLE 5

Solutions in distilled water of the reductive alkylation product of Amine HPA-X and methyl isoamyl ketone (Example 2) were prepared and their dynamic surface tension properties were measured using the procedure described above. The data are set forth in Table 2. Concentrations are tabulated on a 100% active basis.

TABLE 2

| Concentration | HPA-X/MIAK. | | | | |
|---|---|---|---|---|---|
| | Dynamic Surface Tension (dyne/cm) | | | | |
| (wt %) | 0.1 b/s | 1 b/s | 6 b/s | 15 b/s | 20 b/s |
| 0.03 | 33.6 | 42.2 | 53.4 | 59.4 | 59.8 |
| 0.05 | 30.0 | 36.1 | 45.8 | 52.5 | 52.9 |
| 0.07 | 29.5 | 33.0 | 42.4 | 48.3 | 49.8 |
| 0.1 | 29.0 | 31.7 | 39.8 | 45.0 | 46.0 |
| 0.2 | 28.2 | 29.9 | 39.1 | 39.1 | 40.5 |

These results show that the reductive alkylation product of Amine HPA-X and methyl isoamyl ketone exhibited an outstanding ability to reduce the surface tension of water under conditions of both high and low surface creation rate, and that the material was very efficient at reducing the surface tension of water. The low amounts of this material required to provide a reduction in surface tension would positively impact the economics of coating, ink, and agricultural formulations. Furthermore, use of lower surfactant quantities would also reduce emissions of volatile organic compounds from these formulations.

EXAMPLE 6

Solutions in distilled water of the reductive alkylation product of commercial triethylenetetramine mixture (TETA) and methyl isobutyl ketone (Example 3) were prepared and their dynamic surface tension properties were measured using the procedure described above. The data are set forth in Table 3.

TABLE 3

| Concentration | TETA/MIBK. | | | | |
|---|---|---|---|---|---|
| | Dynamic Surface Tension (dyne/cm) | | | | |
| (wt %) | 0.1 b/s | 1 b/s | 6 b/s | 15 b/s | 20 b/s |
| 0.1 | 38.9 | 42.9 | 45.3 | 46.7 | 47.2 |
| 0.2 | 34.5 | 37.2 | 40.5 | 42.5 | 42.2 |
| 0.5 | 30.5 | 31.9 | 34.3 | 36.4 | 36.9 |

These results show that higher polyamines are suitable for use in this invention and that reductive alkylation products of both linear and branched polyamines are active. At a use level of 0.5 wt %, the performance of this material was very good.

The ability of a surfactant in aqueous systems to reduce surface tension under both equilibrium and dynamic conditions is of great importance in the performance of water-based coatings, inks, adhesives, and agricultural formulations. Low equilibrium surface tension allows the development of excellent properties subsequent to application. Low dynamic surface tension results in enhanced wetting and spreading under the dynamic conditions of application, resulting in more efficient use of the formulations and fewer defects. In waterborne coatings, inks, adhesives, and agricultural formulations, the formation of foam is generally undesirable because it complicates handling and can cause defects or result in inefficient application.

STATEMENT OF INDUSTRIAL APPLICATION

The invention provides material suitable for reducing the equilibrium and dynamic surface tension in water-based compositions. CLAIMS

We claim:

1. In a method for applying a water-based composition to a surface, the composition containing an organic compound and an effective amount of a surfactant low foaming for reducing the dynamic surface tension of the composition, the improvement which comprises employing as the surfactant at least one alkylated polyamine compound of the following structures I and II

   I where the R groups are independently hydrogen or C5 to C8 alkyl, provided that at least one R is not hydrogen; n is 2 to 6 and p is 2 to 8, and

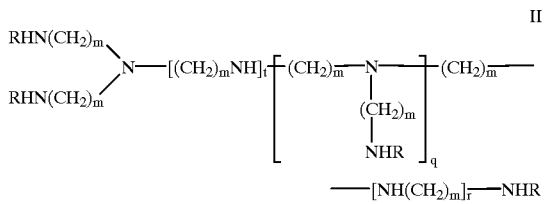

$$\text{II}$$

where the R groups are independently hydrogen or C5 to C8 alkyl, provided at least one R is not hydrogen, m is 2 to 6, t is 0 to 3, q is 0 to 3, and r is 0 to 5.

2. The method of claim 1 in which an aqueous solution of the alkylated polyamine demonstrates a dynamic surface tension of less than 45 dynes/cm at a concentration of ≦5 wt % in water at 23° C. and 1 bubble/second according to the maximum-bubble-pressure method.

3. The method of claim 2 in which the alkylated polyamine is represented by structure I and R is a C5 to C8 alkyl group, n is 2 or 3, and p is 2 to 5.

4. The method of claim 3 in which p is 2 or 3.

5. The method of claim 2 in which the alkylated polyamine is represented by structure II and R is a C5 to C8 alkyl group, m is 2 or 3, t is 0 or 1, q is 0 to 2, and r is 0 to 3.

6. The method of claim 1 in which the alkylated polyamine is the reductive alkylation product of triethylene-tetramine and methyl isobutyl ketone.

7. The method of claim 1 in which the alkylated polyamine is the reductive alkylation product of a mixture of linear and branched tetraethylene pentamine and pentaethylene hexamine and methyl isobutyl ketone.

8. The method of claim 1 in which the alkylated polyamine is the reductive alkylation product of a mixture of linear and branched tetraethylene pentamine and pentaethylene hexamine and methyl isoamyl ketone.

9. The method of claim 1 in which the alkylated polyamine is the reductive alkylation product of a mixture of linear and branched triethylenetetramine, tetraethylene pentamine and pentaethylene hexamine and methyl isoamyl ketone.

10. The method of claim 1 in which the alkylated polyamine is the reductive alkylation product of a mixture of linear and branched triethylenetetramine, tetraethylene pentamine, pentaethylene hexamine, hexaethylene heptamine and heptaethylene octamine and methyl isobutyl ketone.

11. The method of claim 2 in which the measurement is made at 20 bubbles/second.

12. An aqueous composition comprising an organic compound and an effective amount of low foaming alkylated polyamine for reducing the dynamic surface tension of the composition, the alkylated polyamine compound having structure I or I:

where the R groups are independently hydrogen or C5 to C8 alkyl provided that at least one R is hot hydrogen; n is 2 to 6 and p is 2 to 8, and

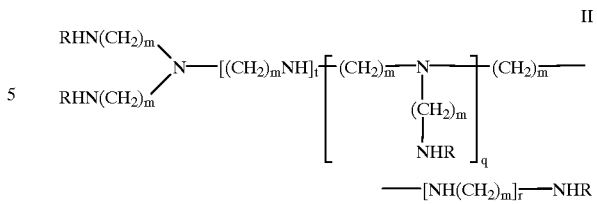

$$\text{II}$$

where the R groups are independently hydrogen or C5 to C8 alkyl, provided at least one R is not hydrogen, m is 2to 6, t is 0 to 3, q is 0 to 3, and r is 0 to 5.

13. The composition of claim 12 in which an aqueous solution of the alkylated polyamine demonstrates a dynamic surface tension of less than 45 dynes/cm at a concentration of ≦5 wt % in water at 23° C. and 1 bubble/second according to the maximum-bubble-pressure method.

14. The composition of claim 13 in which the alkylated polyamine is represented by structure I and R is a C5 to C8 alkyl group, n is 2 or 3, and p is 2 to 5.

15. The composition of claim 14 in which p is 2 or 3.

16. The composition of claim 13 in which the alkylated polyamine is represented by structure II and R is a C5 to C8 alkyl group, m is 2 or 3, t is 0 or 1, q is 0 to 2, and r is 0 to 3.

17. The composition of claim 12 in which the alkylated polyamine is the reductive alkylation product of triethylene-tetramine and methyl isobutyl ketone.

18. The composition of claim 12 in which the alkylated polyamine is the reductive alkylation product of a mixture of linear and branched tetraethylene pentamine and pentaethylene hexamine and methyl isobutyl ketone.

19. The composition of claim 12 in which the alkylated polyamine is the reductive alkylation product of a mixture of linear and branched tetraethylene pentamine and pentaethylene hexamine and methyl isoamyl ketone.

20. The composition of claim 12 in which the alkylated polyamine is the reductive alkylation product of a mixture of linear and branched triethylenetetramine, tetraethylene pentamine and pentaethylene hexamine and methyl isoamyl ketone.

21. The composition of claim 12 in which the alkylated polyamine is the reductive alkylation product of a mixture of linear and branched triethylenetetramine, tetraethylene pentamine, pentaethylene hexamine, hexaethylene heptamine and heptaethylene octamine and methyl isobutyl ketone.

22. The composition of claim 12 which is an organic coating composition of 30 to 80 wt % components, which components comprise 0 to 50 wt % pigment dispersant, grind resin or mixtures thereof;

0 to 80 wt % coloring pigment, extender pigment, anti-corrosive pigment, other pigment types or mixtures thereof;

5 to 99.9 wt % water-borne, water-dispersible or water-soluble resin or mixtures thereof;

0 to 30 wt % slip additive, antimicrobial agent, processing aid, defoamer or mixtures thereof;

0 to 50 wt % coalescing or other solvents;

0.01 to 10 wt % surfactant, wetting agent, flow and leveling agents or mixtures thereof; and 0.01 to 5 wt % alkylated polyamine.

23. The composition of claim 12 which is an ink composition of 20 to 60 wt % components, which components comprise 1 to 50 wt % pigment;

0 to 50 wt % pigment dispersant, grind resin or mixtures thereof;

0 to 50 wt % clay base in a resin solution vehicle;

5 to 99 wt % water-borne, water-dispersible or water-soluble resin or mixtures thereof;

0 to 30 wt % coalescing solvent;

0.01 to 10 wt % processing aid, defoamer, solubilizing agent or mixtures thereof;

0.01 to 10 wt % surfactant, wetting agent or mixtures thereof; and 0.01 to 5 wt % alkylated polyamine.

24. The composition of claim 12 which is an agricultural composition of 0.1 to 80 wt % components, which components comprise 1 to 50 wt % pesticide, plant growth modifying agent or mixtures thereof;

0 to 5 wt % dye;

0 to 20 wt % thickener, stabilizer, co-surfactant, gel inhibitor, defoaming agent or mixtures thereof;

0 to 25 wt % antifreeze;

0 to 50 wt % coalescing or other solvents;

0.01 to 10 wt % surfactant; and 0.1 to 50 wt % alkylated polyamine.

* * * * *

UNITED STATES PATENT AND TRADEMARK OFFICE
CERTIFICATE OF CORRECTION

PATENT NO. : 6,015,852

DATED : 18 January 2000

INVENTOR(S) : Kevin Rodney Lassila, Kristen Elaine Minnich and Richard Van Court Carr It is certified that error appears in the above-identified patent and that said Letters Patent is hereby corrected as shown below:

Column 10, line 56 should read: ... amount of low foaming surfactant for

Column 11, line 66 should read: . . .R is not hydrogen; n is 2 to

Signed and Sealed this

Seventeenth Day of October, 2000

Attest:

Attesting Officer

Q. TODD DICKINSON

Director of Patents and Trademarks

UNITED STATES PATENT AND TRADEMARK OFFICE
CERTIFICATE OF CORRECTION

PATENT NO. : 6,015,852
DATED : January 18, 2000
INVENTOR(S) : Kevin Rodney Lassila et al.

It is certified that error appears in the above-identified patent and that said Letters Patent is hereby corrected as shown below:

Column 11,
Line 61, delete "I or I:" and substitute therefor -- I or II:. --

Signed and Sealed this

Ninth Day of November, 2004

JON W. DUDAS
*Director of the United States Patent and Trademark Office*